United States Patent [19]

Talbot et al.

[11] Patent Number: 4,775,407

[45] Date of Patent: Oct. 4, 1988

[54] METHOD OF TREATING SURFACES TO CONTROL BRYOPHYTES OR LICHENS USING A WATER SOLUBLE TETRAKIS (HYDROXYMETHYL) PHOSPHONIUM SALT

[75] Inventors: Robert E. Talbot, Cannock; Kenneth G. Cooper, Hagley, both of England

[73] Assignee: Albright & Wilson Limited, Warley, England

[21] Appl. No.: 930,316

[22] Filed: Nov. 12, 1986

[30] Foreign Application Priority Data

Nov. 11, 1985 [GB] United Kingdom ................ 8527793

[51] Int. Cl.$^4$ .......................................... A01N 57/20
[52] U.S. Cl. ......................................... 71/87; 71/86; 71/67; 514/129
[58] Field of Search ................ 71/67, 86, 87; 514/129

[56] References Cited

U.S. PATENT DOCUMENTS 3,704,325 11/1972 Stockel et al.
4,673,509 6/1987 Davis et al.

FOREIGN PATENT DOCUMENTS

| 0000694 | 2/1979 | European Pat. Off. |
| 0105843 | 4/1983 | European Pat. Off. |
| 0139404 | 5/1985 | European Pat. Off. |
| 1251235 | 12/1960 | France |
| 1251094 | 12/1960 | France |
| 2136433 | 9/1984 | United Kingdom |
| 2145708 | 4/1985 | United Kingdom |

OTHER PUBLICATIONS

Davis et al., Eur. Pat. Appl. 139,404, Chem. Abst. vol. 103(1985), 100400w.

Davis et al., GB 2,145,708, Chem. Abst., vol. 103(1985), 128751h.

*Primary Examiner*—Catherine L. Mills
*Attorney, Agent, or Firm*—Frishauf, Holtz, Goodman & Woodard

[57] ABSTRACT

A method of treating surfaces colonized or colonizable by bryophites or lichens which comprises applying thereto sufficient of a water soluble tetrakis (hydroxymethyl) phosphonium salt to kill, or inhibit the growth thereon of said bryophytes or lichens.

10 Claims, No Drawings

METHOD OF TREATING SURFACES TO CONTROL BRYOPHYTES OR LICHENS USING A WATER SOLUBLE TETRAKIS (HYDROXYMETHYL) PHOSPHONIUM SALT

The present invention provides a novel composition and method for controlling or killing or inhibiting the growth of bryophytes (e.g. mosses and liverworts), lichens, sessile algae and fungal, viral, bacterial and other microbial plant pathogens. It is applicable to the killing of these organisms in lawns, gardens, orchards or agricultural land, hydroponic beds or forests and upon higher plants, e.g. crops and on paths, roads, walls, woodwork, brickwork and other structures without substantial detriment to grass or most broad leaf plants.

European Patent Specification No. 0139404 A1 described the use of certain hydroxyalkyl phosphine derivatives as biocides in water treatment, and for the preservation of aqueous products.

We have now discovered that when aqueous solutions of hydroxyalkyl phosphine derivatives are applied to mosses, liverworts or lichens, or to soil or plants infected with or susceptible to fungal or microbial plant pathogens, the moss, lichens or pathogens are killed or substantially reduced compared with similar untreated loci, while grasses and most broad leaved plants are relatively unaffected.

According to our invention hydroxyalkyl phosphine compounds, preferably of the formula: $[HORPR'_n]_y X_x$, wherein n is 2 or 3; x is 0 or 1 such that $(n+x)=2$ or 4; y is equal to the valency of X; R is an alkylene group of 1 to 4 carbon atoms; each R' may be the same or different and represents an alkyl or alkenyl group having up to 24 carbon atoms or a group of the formula HOR—, wherein R is as defined above; and X is an anion such that the phosphorus compound is water soluble; or water soluble condensates of the aforesaid hydroxyalkyl phosphine compounds; are used to control bryophytes, lichens, sessile algae, or fungal or microbial plant pathogens.

We prefer compounds in which $n=3$ and especially compounds in which at least 2 and preferably 3 R' groups are HOR groups. We particularly prefer compounds in which each R is a methylene group. Thus we strongly prefer water-soluble tetrakis(hydroxymethyl)-phosphonium salts (herein referred to as "THP salts"). The compound tris(hydroxymethyl)phosphine is also effective, but is generally insufficiently stable in marketable formulations to be of commercial interest in itself. However any precursor which yields tris(hydroxymethyl)phosphine at the desired locus may be used according to our invention.

The preferred tetrakis(hydroxymethyl)phosphonium compounds are tetrakis(hydroxymethyl)phosphonium sulphate and the corresponding chloride, bromide and phosphate, however X may be any compatible anion such as nitrate, fluoride, phosphonate, nitrite, sulphite, phosphite, iodide, borate or carbonate or an organic anion such as formate, acetate, benzoate, citrate, tartrate, lactate, propionate, butyrate or a surfactant anion such as an alkyl benzene sulphonate, or alkyl ether sulphate.

The hydroxyalkyl phosphine compound may alternatively contain 2 or more phosphorus atoms, and preferably the phosphorus compound is water soluble to a concentration of at least 0.5 g/l at 25° C. Such phosphorus compounds contain at least 1 hydroxyalkyl group, usually per phosphorus atom, and preferably at least 2 hydroxyalkyl groups per phosphorus atom. Such hydroxyalkyl groups are preferably of formula ROH, where R is as defined above. The group or groups joining the phosphorus atoms together may be of formula —R—, —R—O—, —R—O—R— or —R—NH—R or —R—R''—R— where R is as defined above and R'' is the residue formed by removal of two hydrogen atoms, bonded to nitrogen, from a di or polyamide or di or poly amine, such as urea, dicyandiamide, thiourea or guanidine. Such compounds with 2 or more, e.g. 3, hydroxyalkyl groups per phosphorus atom may be made by self condensation of compounds with 3 or 4 hydroxyalkyl groups attached to one phosphorus atom, e.g. of formula $[HORPR'_n O_m]_y X_x$ or with a compound of the formula $R''H_2$ such as urea. Condensation may be performed by heating at 40°-120° C.

According to a further embodiment our invention provides a composition adapted for use in controlling bryophytes, lichens or fungal or microbial plant pathogens which contains an effective amount of a hydroxyalkyl phosphine compound as aforesaid together with a horticulturally or agriculturally acceptable diluent, carrier and/or solvent therefore.

The hydroxyalkyl phosphine compounds may be present as a solution in water at effective concentrations up to saturation. They will usually be supplied as concentrates at about 50 to 80% by weight THP concentration, eg. 75% by wt. but will normally be diluted to a concentration of from 0.01 to 10% by wt. before application. Alternatively they may be admixed with or adsorbed upon inert, particulate, non-phytotoxic solids such as talc or dissolved in organic solvents or suspended in or as dispersions or emulsions. They may be used in conjunction with other mosskillers or biocides, such as herbicides, fungicides, bactericides, insecticides and weedkillers, or with surfactants, wetting agents, adhesives, emulsifiers, suspending agents, thickeners, synergists, hormones, plant growth regulators or plant nutrients.

The compositions of our invention may be applied to lawns, flower or vegetable beds, arable land, meadowland, orchards or woodland, or hydroponic beds, or to the seeds, roots, leaves, flowers, fruit and/or stems of plants, or to paths, roads, walls, woodwork, brickwork or similar invasible surfaces.

The compositions may be of value, inter alia, in controlling moss or sessile algae in lawns or on paths or walks, as seed dressings, as sprays for controlling fungal, bacterial or viral infections on leaves, flowers and fruit, such as mildew, botrytis, rust, fusarium, mosaic diseases or wilt, for application to soil or to the roots of seedlings (e.g. of brassica seedlings to inhibit club root) and in the control of nunerous fungal, viral, protozoal and bacterial diseases of plants, including fungal blights such as potatoe blight, cankers such as apple canker, scabs, root rot, and base rot of bulbs. The compositions are especially effective in protecting cereal crops including wheat, barley, rye, oats, rice, maize, millet and sesame against a broad spectrum of plant diseases.

Other crops of importance which may be protected according to our invention include sugar cane, root vegetables including carrots, parsnips, turnips, beetroot, sugar beet, radishes, swedes and mangolds, brassicas including cabbages, broccoli, cauliflower and sprouts; grazing land, pulses including peas, broad beans, French beans, runner beans, navy beans, kidney beans and lentils; curcubaceous plants including cucumbers, marrows, gourds and squashes, oilseed rape, timber, rubber, cotton, coffee, cocoa, jute, tomatoes, potatoes, yams, tobacco, bananas, coconut palm, olives, alliums including onions, shallots, leeks, garlic, chives and spring onions, ground nuts, peanuts, sorghum, oil palm, roses, hemp, flax, lucerne, alfalfa, tea and fruit, including citrus fruit, apples, plums, peaches, nectarines, mangoes, pears, cherries, grapes, berries, currants, dates, figs, avocados, almonds, and apricots.

The invention is illustrated by the following examples:

EXAMPLE 1

The following test was carried out using a 75% solution of tetrakis(hydroxymethyl)phosphonium sulphate, which solution is referred to hereinafter as THPS.

A solution, containing 5 ml of THPS per liter of water was sprayed onto part of a moss colony growing on a damp stone wall. Within 24 hours whilst the unsprayed part of the colony was still luxuriant and green, the sprayed area had begun to turn brown and contract. Within 48 hours, the sprayed area was obviously dead (i.e. it was completely brown and had contracted considerably) whilst the unsprayed area was unaffected.

EXAMPLE 2

Example 1 was repeated using a solution containing 5 ml THPS per liter of water and neutralising the solution to a pH between 7 and 8 with sodium bicarbonate before spraying. The results obtained were substantially the same as those reported in Example 1.

EXAMPLE 3

THPS solutions were tested for their effectiveness at killing moss colonies growing between broadleafed plants and grasses.

Solutions containing 5 ml THPS per liter of water (both neutralised with sodium bicarbonate and unneutralised) were sprayed onto separate areas. Also solutions containing 3.75 ml THPS per liter of water were applied to other areas using a watering can.

In all cases after 24-48 hours, the treated moss had been killed. Broadleafed plants were not significantly affected and grasses showed no sign of any adverse effect compared with untreated grasses.

EXAMPLE 4

When examples 1 to 3 are repeated using THP chloride, THP phosphate or THP phosphite, substantially similar results are obtained.

EXAMPLE 5

When THPS in a concentration of 5 mls per liter of water is sprayed onto roses showing early signs of black spot and mildew in three applications at 48 hour intervals and the treated roses are compared with an untreated control bed, the treated plants exhibit substantially less symptoms of both diseases than the control plants.

EXAMPLE 6

When plots of wheat are sprayed with aqueous THPS at 5 mls per liter of water incidence of fungal, viral and microbial diseases including yellow and brown rust, mildew, septoria and eyespot infections are materially reduced compared to control plots.

EXAMPLE 7

When THPS adsorbed on talc is applied to a variety of seeds as a seed dressing, incidence of fungal, bacterial and viral infections in plants grown from the seed is decreased compared with untreated seed.

We claim:

1. A method of treating surfaces colonised or colonisable by bryophites or lichens which comprises applying thereto sufficient of a water soluble tetrakis(hydroxymethyl)phosphonium salt to kill, or inhibit the growth thereon of said bryophites or lichens.

2. The method of claim 1 wherein said water soluble tetrakis(hydroxymethyl)phosphonium salt is applied to lawns to kill moss.

3. The method of claim 2 wherein said salt is the sulphate.

4. The method of claim 2 wherein said salt is the chloride.

5. The method of claim 2 wherein said salt is the bromide.

6. The method of claim 2 wherein said salt is the phosphate.

7. The method of claim 1 wherein said salt is the sulphate.

8. The method of claim 1 wherein said salt is the chloride.

9. The method of claim 1 wherein said salt is the bromide.

10. The method of claim 1 wherein said salt is the phosphate.

* * * * *